US012788353B2

(12) United States Patent
Wang et al.

(10) Patent No.: US 12,788,353 B2
(45) Date of Patent: Nov. 10, 2026

(54) DATA LINK DETECTION METHOD, PET/CT IMAGING SYSTEM AND READABLE STORAGE MEDIUM

(71) Applicant: Shanghai United Imaging Healthcare Co., Ltd., Shanghai (CN)

(72) Inventors: Kang Wang, Shanghai (CN); Xu Liu, Shanghai (CN)

(73) Assignee: Shanghai United Imaging Healthcare Co., Ltd., Shanghai (CN)

( * ) Notice: Subject to any disclaimer, the term of this patent is extended or adjusted under 35 U.S.C. 154(b) by 127 days.

(21) Appl. No.: 18/991,804

(22) Filed: Dec. 23, 2024

(65) Prior Publication Data

US 2025/0204881 A1 Jun. 26, 2025

(30) Foreign Application Priority Data

Dec. 21, 2023 (CN) ......................... 202311775106.4

(51) Int. Cl.
*A61B 6/03* (2006.01)
*A61B 6/00* (2006.01)
*G01T 1/29* (2006.01)

(52) U.S. Cl.
CPC ................ *A61B 6/56* (2013.01); *A61B 6/032* (2013.01); *A61B 6/037* (2013.01); *G01T 1/2985* (2013.01); *A61B 6/4417* (2013.01)

(58) Field of Classification Search
CPC ........... A61B 6/56; A61B 6/032; A61B 6/037; A61B 6/4417; A61B 6/58; A61B 6/5235; A61B 6/563; G01T 1/2985
See application file for complete search history.

(56) References Cited

U.S. PATENT DOCUMENTS 4,796,183 A * 1/1989 Ermert .................... H01P 1/068
378/10

FOREIGN PATENT DOCUMENTS

| | | |
|---|---|---|
| CN | 108022637 A | 5/2018 |
| CN | 104702489 B | 8/2019 |
| CN | 115736958 A | 3/2023 |

OTHER PUBLICATIONS

Imrek et al., "Distributed Online Coincidence Detection Using IP Multicast for the miniPET-II Detector", 2009 IEEE Nuclear Science Symposium Conference Record, J05-12, 3 pages. (Year: 2009).*

* cited by examiner

*Primary Examiner* — Kiho Kim

(57) ABSTRACT

A data link detection method is disclosed. The method includes: determining a target data sub-link in a data link, the data link including at least one data sub-link; sending a detection instruction to a sending component in the target data sub-link to instruct the sending component to send detection data to a receiving component in the target data sub-link for detection; and receiving a detection result corresponding to the target data sub-link. A PET/CT imaging system and a readable storage medium are disclosed.

20 Claims, 5 Drawing Sheets

DATA LINK DETECTION METHOD, PET/CT IMAGING SYSTEM AND READABLE STORAGE MEDIUM

CROSS-REFERENCE TO RELATED APPLICATIONS

The present application claims priority to Chinese patent application No. 202311775106.4, filed on Dec. 21, 2023, the entire contents of which are incorporated herein by reference.

TECHNICAL FIELD

The present disclosure relates to the field of medical device technologies, and in particular, to a data link detection method, a PET/CT imaging system and a readable storage medium.

BACKGROUND

A multimodality imaging scanners combining positron emission tomography (PET) and computed tomography (CT) has led to a new paradigm in image display and presentation that raises new challenges in workstation interpretation software, image navigation, and communication. When performing a medical imaging scan, a positron radionuclide tracer is injected into a patient, and then CT imaging and PET imaging are performed on the patient, respectively. Further, a CT image and a PET image are registered and fused to obtain a final medical scanning image.

During the scanning, the PET/CT device transmits acquired raw CT data and raw PET data to a reconstruction host through respective data links, and then the reconstruction host performs data parsing during reconstruction. If the data is missing or wrong after parsing, an error is reported, indicating that the data link may be abnormal in this time.

Based on this, how to detect the data link in a PET/CT system before the image scanning to avoid scanning failure due to data link abnormalities has become a technical problem that needs to be solved urgently.

SUMMARY

Based on this, it is necessary to provide a data link detection method and device, a computer device, a computer-readable storage medium, and a computer program product that can detect the data link of the PET/CT system in response to the above technical problems.

A first aspect of the present disclosure provides a data link detection method. The method including: determining a target data sub-link in a data link; the data link including at least one data sub-link; sending a detection instruction to a sending component in the target data sub-link to instruct the sending component to send detection data to a receiving component in the target data sub-link for detection; and receiving a detection result corresponding to the target data sub-link.

In the first aspect of the present disclosure, the data link includes a detector data sub-link, a coincidence process and control board data sub-link, and an acquisition card data sub-link. The detector data sub-link includes at least one detector module, and each detector module includes a plurality of detector units. The coincidence process and control board data sub-link includes the at least one detector module and at least one coincidence process and control board correspondingly connected to the at least one detector module. The acquisition card data sub-link includes at least one coincidence process and control board and at least one data acquisition card connected to the at least one coincidence process and control board respectively.

In the first aspect of the present disclosure, sending the detection instruction to the sending component in the target data sub-link to instruct the sending component to send the detection data to the receiving component in the target data sub-link for detection, includes: determining the sending component in the target data sub-link and the receiving component corresponding to the sending component in the target data sub-link; and sending the detection instruction to the sending component to instruct the sending component to send the detection data to the corresponding receiving component for detection.

In the first aspect of the present disclosure, the target data sub-link is the detector data sub-link, determining the sending component in the target data sub-link and the receiving component corresponding to the sending component in the target data sub-link includes: determining, for the plurality of detector units in each detector module, a detector unit in the detector module as the sending component; and determining another detector unit corresponding to the detector unit in the detector module as the receiving component corresponding to the sending component.

In the first aspect of the present disclosure, the target data sub-link is the coincidence process and control board data sub-link, determining the sending component in the target data sub-link and the receiving component corresponding to the sending component in the target data sub-link includes: determining, for each detector module, the detector module as the sending component; and determining the coincidence process and control board connected to the detector module as the receiving component corresponding to the sending component.

In the first aspect of the present disclosure, the target data sub-link is the acquisition card data sub-link, determining the sending component in the target data sub-link and the receiving component corresponding to the sending component in the target data sub-link includes: determining, for each coincidence process and control board, the coincidence process and control board as the sending component; and determining the acquisition card connected to the coincidence process and control board as the receiving component corresponding to the sending component.

In an embodiment, the target data sub-link is the acquisition card data sub-link, and the acquisition card data sub-link includes coincidence process and control boards that are communicatively connected in sequence, determining the sending component in the target data sub-link and the receiving component corresponding to the sending component in the target data sub-link includes: determining, for each coincidence process and control board, the coincidence process and control board as the sending component; determining an adjacent coincidence process and control board adjacent to and communicatively connected to the coincidence process and control board; and determining the acquisition card connected to the adjacent coincidence process and control board as the receiving component corresponding to the sending component.

A second aspect of the present disclosure further provides a data link detection device. The device includes: a determination module configured to determine a target data sub-link in a data link; the data link including at least one data sub-link; a sending module configured to send a detection instruction to a sending component in the target data sub-link to instruct the sending component to send detection data to a receiving component in the target data sub-link for detection; and a receiving module configured to receive a detection result corresponding to the target data sub-link.

A third aspect of the present disclosure further provides a PET/CT imaging system, including a PET scanner, a computer device, and a display device. The PET scanner includes a plurality of detector rings arranged in an axial direction, and each detector ring is connected to the computer device via a data link. The computer device including a processor and a memory storing a computer program. When the processor executes the computer program, steps of the data link detection method in the first aspect are implemented.

A fourth aspect of the present disclosure further provides a non-transitory computer-readable storage medium having a computer program stored therein. When the computer program is executed by a processor, steps of the data link detection method in the first aspect are implemented.

A fifth aspect of the present disclosure further provides a computer program product, including a computer program. When the computer program is executed by a processor, steps of the data link detection method in the first aspect are implemented.

BRIEF DESCRIPTION OF THE DRAWINGS

In order to describe the technical solutions of the embodiments of the present disclosure or the related art more clearly, the accompanying drawings required for describing the embodiments or for describing the related art will be briefly introduced as follows. Apparently, the accompanying drawings, in the following description, illustrate merely some embodiments of the present disclosure, for a person of ordinary skill in the art, other drawings can also be obtained according to these accompanying drawings without making any creative efforts.

DETAILED DESCRIPTION OF THE EMBODIMENTS

In order to make the objectives, technical solutions and advantages of the present disclosure more clearly understood, the application will be further described in detail with the accompanying drawings and embodiments. It should be understood that the specific embodiments described herein are only used to explain the application and not to limit the application.

In the medical field, for a PET/CT system, when a PET/CT scan is performed in a clinical scenario, a patient is first injected with a drug (such as a positron radionuclide tracer). After the patient has metabolized the injected drug for a period of time, the patient is scanned by CT and then by PET using the PET/CT system. During the scanning, the PET/CT system performs data parsing when reconstructing after acquiring data. If the data is missing or wrong during the parsing, an error is reported. In this case, the system needs to be restarted or an engineer needs to be contacted for repair, resulting in the failure of the scan. In this case, the patient needs to be re-scanned the next day, or the patient who has already injected the drug on the same day needs to be transferred to another site for re-scanning. However, whether the scan is performed the next day or the patient is currently transferred to another site for re-scanning, the patient will be exposed to more radiation and equipment resources will be wasted. Therefore, it is very necessary to ensure that there is no problem with a PET data link before performing a PET scan.

Based on this, an embodiment of the present disclosure provides a data link detection method, which is applied to detecting the PET data link. In addition, this method is also applied to detecting a CT data link, or detecting other data links in other medical scanning devices. For example, data links of multimodal imaging devices such as, MRI/PET, etc. The embodiment of the present disclosure does not specifically limit the application objects and application scenarios of this method. In addition, by using this data link detection method, the data link corresponding to the medical scan can be detected before the medical scan is performed, thereby ensuring the reliability of the data link. Exemplarily, the detection for the data link may be automatically triggered at a certain time interval, or the detection for the data link may also be manually triggered. A triggering manner and a triggering time of the detection for the data link are not specifically limited in the embodiments of the present disclosure.

Figure 1:
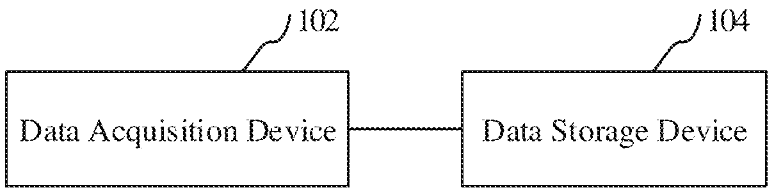
FIG. 1 is a diagram illustrating an application environment of a data link detection method in an embodiment.

The data link detection method provided in the embodiment of the present disclosure may be applied to an application environment shown in FIG. 1. A data acquisition system may include a data acquisition device 102 and a data storage device 104. There is at least one data transmission link between the data acquisition device 102 and the data storage device 104, and the data acquisition device 102 transmits the acquired data to the data storage device 104 through the at least one data transmission link.

Exemplarily, when detecting the at least one data transmission link between the data acquisition device 102 and the data storage device 104, a data transmission may be performed based on detection data to detect the data transmission link. Optionally, the detection data may be preset analog data, or may be data actually acquired by the data acquisition device 102. The preset analog data may be analog data of a preset type, a preset format, a preset rate, a preset duration, or the like.

Exemplarily, in a case that the detection data is the data actually acquired by the data acquisition device 102, a detection mark may be added to the data actually acquired by the data acquisition device 102 during the data transmission, so that after receiving the data by using the data transmission link, the data storage device 104 can perform data anomaly determination based on the detection mark carried in the data, thereby improving the accuracy and efficiency of data anomaly determination. The information marked by the detection mark may be a preset type, a preset format, a preset rate, a preset duration, or the like.

As an example, the data acquisition device 102 may include a medical imaging scanning device, and the data storage device 104 may include a host that is communicatively connected to the medical imaging scanning device. The medical imaging scanning device may perform a medical imaging scan on a to-be-detected object to obtain original scanning data of the to-be-detected object, and transmit the original scanning data to the host through the at least one data transmission link, so that the host stores the original scanning data. Exemplarily, the host may also perform medical imaging reconstruction based on the original scanning data to obtain a medical scanning image.

For example, in a case that the medical imaging scanning device is a PET/CT device, the PET/CT device may include a CT data link and a PET data link, and the host that is communicatively connected to the PET/CT device may include one or two. In other words, the PET/CT device may be connected to a host via the CT data link, or may be connected to this host via the PET data link. In this host, both CT scanning data and PET scanning data may be stored. Alternatively, the PET/CT device may be connected to a first host storing CT scanning data via the CT data link, and may be connected to a second host storing PET scanning data via the PET data link.

It should be noted that the above example is only used as an illustrative example. In an actual application, the host that is communicatively connected to the medical imaging scanning device may include one or more hosts, and in addition to the host, may also include one or more backup machines. For example, the PET/CT device may be connected to the host or the backup machine through the PET data link. A connection manner of the data storage system is not specifically limited in the embodiments of the present disclosure.

In addition, the data storage device may be any type of terminal, any type of server, or the like, and the embodiments of the present disclosure do not specifically limit thereto.

Figure 2:
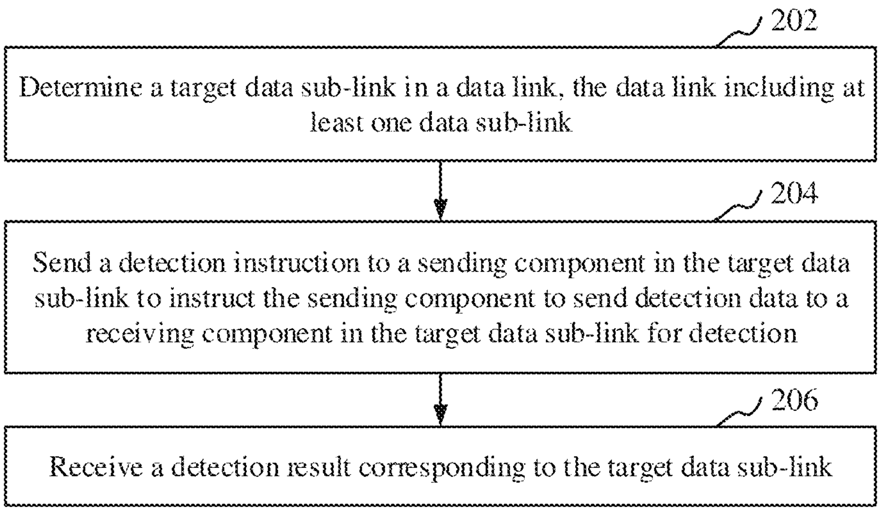
FIG. 2 is a flow diagram illustrating a data link detection method in an embodiment.

In an exemplary embodiment, as shown in FIG. 2, a data link detection method is provided. An example where the method is applied to the data acquisition system in FIG. 1 is taken for illustration, and the method includes the following steps 202 to 206.

In step 202, a target data sub-link in a data link is determined. The data link includes at least one data sub-link.

The data link may be a data transmission link between the data acquisition device and the data storage device in the data acquisition system. Between the data acquisition device and the data storage device, one or more types of data links may be included, and the same data link may also include one or more data sub-links. The at least one data sub-link corresponds to a coincidence event belonging to a single detector ring, or to a coincidence event belonging to different detector rings. Therefore, the detection for the data link may be a coincidence detection in the same detector ring or a cross-ring coincidence detection of different detector rings.

Exemplarily, in a case that the data link includes a plurality of data sub-links, the plurality of data sub-links may be parallel data sub-links, i.e., each of the data sub-links is connected to the data acquisition device and the data storage device, respectively. In addition, the plurality of data sub-links may also be serial data sub-links, i.e., all data sub-links are sequentially connected in series to form a data transmission link between the data acquisition device and the data storage device. Moreover, the plurality of data sub-links may also be connected in a parallel and serial cross manner to form a data transmission link between the data acquisition device and the data storage device.

As an example, the data link between the PET/CT device and the host may include a CT data link and/or a PET data link. For the PET data link, the PET data link may include a detector data sub-link, a coincidence process and control board data sub-link, and an acquisition card data sub-link. In the PET data link, the PET/CT device may acquire PET scanning data through a detector, send the acquired PET scanning data to a coincidence process and control board through the detector, and then send the PET scanning data to a data acquisition card through the coincidence process and control board. The data acquisition card may be mounted on the host that is communicatively connected to the PET/CT device, so that the data acquisition card can store the acquired PET scanning data in the host.

Exemplarily, when performing a data link detection, a part or all of the data sub-links in the data link can be detected. In addition, when performing the data link detection, a detection time or a detection interval may be preset to automatically trigger the detection for the part or all of the data sub-links in the data link. Alternatively, a manual detection control may also be set to manually trigger the detection for the part or all of the data sub-links in the data link.

As an example, taking the detection of the PET data link in the PET/CT device as an example, a detection operation of the PET data link may be automatically performed before the PET/CT device is started to perform the PET/CT scan. In this case, it is determined that the target data sub-link in the PET data link includes the detector data sub-link, the coincidence process and control board data sub-link, and the acquisition card data sub-link.

As another example, in a case that a data sub-link in the data link is separately triggered, the target data sub-link to be detected in the data link may be determined based on identification information of the data sub-link carried in a trigger instruction. The trigger instruction may carry identification information of one or more data sub-links, so as to trigger a detection operation on one or more target data sub-links. Different identification information is assigned to different data sub-links only to distinguish different data sub-links. The identification information may be set in any appropriate manner as long as the data sub-links can be distinguished, which is not limited thereto in the present disclosure.

In step 204, a detection instruction is sent to a sending component in the target data sub-link to instruct the sending component to send detection data to a receiving component in the target data sub-link for detection.

For the target data sub-link, it may include at least one sending component and a receiving component corresponding to the sending component. One sending component may correspond to one or more receiving components. The receiving components corresponding to different sending components may be the same or different. In an actual application scenario, the sending component in the target data sub-link and the receiving component corresponding to the sending component may be determined according to a link structure of the target data sub-link.

Exemplarily, when detecting the target data sub-link, the detection instruction may be sent to each sending component in the target data sub-link, respectively, so that each sending component in the target data sub-link may send preset detection data to the corresponding receiving component when receiving the detection instruction, thereby achieving the detection for the data transmission link between each sending component and each receiving component. The detection data sent by each sending component to the corresponding receiving component may be the same, and the detection data may be preset analog detection data of a known format, a known rate, and a known duration, which is beneficial for each receiving component to compare the received data with the preset detection data, thereby verifying the stability and accuracy of the data transmission link between the sending component and the receiving component.

In step 206, a detection result corresponding to the target data sub-link is received.

Exemplarily, in a case that the target data sub-link includes the plurality of receiving components, each receiving component may compare the received data with the preset detection data when receiving the data sent by the sending component, so as to obtain the corresponding detection result. Further, each receiving component may report its own detection result, respectively, so that the data acquisition system may obtain the detection result corresponding to the target data sub-link. The detection result corresponding to the target data sub-link may include the detection result of the data transmission link between each sending component and the corresponding receiving component. For example, whether the data transmission link between the sending component a and the receiving component b is normal or abnormal.

Exemplarily, for each receiving component, when performing a data comparison, multiple data comparison forms such as a data missing comparison and a data error comparison may be performed on the received data and the preset detection time. When data comparison results in all forms are normal, it may be determined that the data transmission link between the receiving component and the corresponding sending component is normal. On the contrary, it may be determined that the data transmission link between the receiving component and the corresponding sending component is abnormal. Exemplarily, in a case that the data transmission link is abnormal, a type of anomaly may further be specifically determined, such as a data missing anomaly, or a data error anomaly.

Exemplarily, when the detection result of the data transmission link between each sending component and the corresponding receiving component in the target data sub-link is obtained, the final detection result of the target data sub-link may be further obtained according to the detection result of the data transmission link between each sending component and the corresponding receiving component. For example, when a proportion of normal detection results is greater than a preset number threshold, it may be determined that the final detection result of the target data sub-link is normal. On the contrary, when the proportion of normal detection results is not greater than the preset data threshold, it may be determined that the final detection result of the target data sub-link is abnormal.

Exemplarily, when the detection result of the target data sub-link is obtained, the detection result of the target data sub-link may also be output and displayed. The detection result of the target data sub-link may include the detection result of the data transmission link between each sending component and the receiving component in the target data sub-link, and the final detection result of the target data sub-link.

In the above data link detection method, the target data sub-link in the data link is determined. The data link includes the at least one data sub-link. Then, the detection instruction is sent to the sending component in the target data sub-link to instruct the sending component to send the detection data to the receiving component in the target data sub-link for detection. Further, the detection result corresponding to the target data sub-link is received. In other words, by using the method in the embodiment of the present disclosure, the target data sub-link in the data link required for data acquisition can be automatically detected before the data acquisition is performed, so as to ensure the stability and reliability of the target data sub-link before the data acquisition and transmission are performed based on the target data sub-link, thereby avoiding the data anomaly such as a data missing or a data error in the data transmitted through the target data sub-link, and improving the integrity and accuracy of data transmission. Based on this, when the method provided in the embodiment of the present disclosure is applied to the PET/CT device, each data sub-link used for PET data transmission and/or CT data transmission in the PET/CT device can be detected before the PET/CT scan is performed, thereby avoiding a situation in which the scan fails due to abnormal data caused by problems in the data sub-links during the PET data acquisition and/or CT data acquisition, and also avoiding the patient from being exposed to more electromagnetic radiation, so as to improve the reliability and safety of the PET/CT scan.

Figure 3:
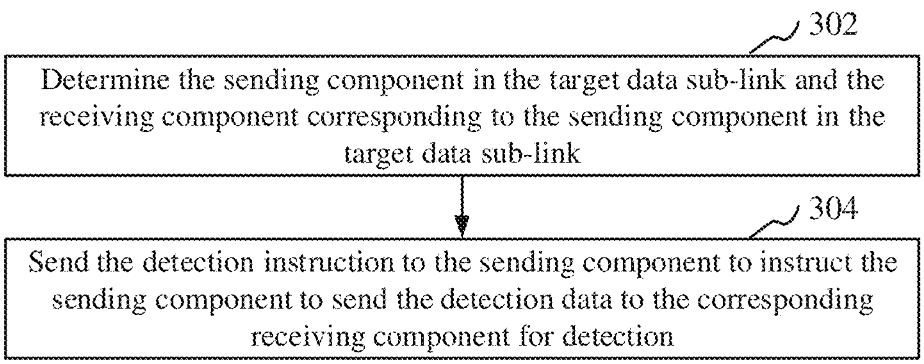
FIG. 3 is a flow diagram illustrating a data link detection method in another embodiment.

In an exemplary embodiment, as shown in FIG. 3, the above step 204 may include steps 302 to 304.

In step 302, the sending component in the target data sub-link and the receiving component corresponding to the sending component in the target data sub-link are determined.

In step 304, the detection instruction is sent to the sending component to instruct the sending component to send the detection data to the corresponding receiving component for detection.

Exemplarily, in this example, in a case that the target data sub-link to be detected in the data link is determined, the sending component and the receiving component corresponding to the sending component in the target data sub-link may be further determined according to the link structure of the target data sub-link. In this way, after the sending component in the target data sub-link is determined, the detection instruction may be sent to the sending component in the target data sub-link to instruct the sending component to send preset detection data to the corresponding receiving component, so as to detect the data transmission link between the sending component and the receiving component.

As an example, the PET data link in the PET/CT device is used as an example for description. Exemplarily, the PET data link may include the detector data sub-link, the coincidence process and control board data sub-link, and the acquisition card data sub-link.

Figure 4:
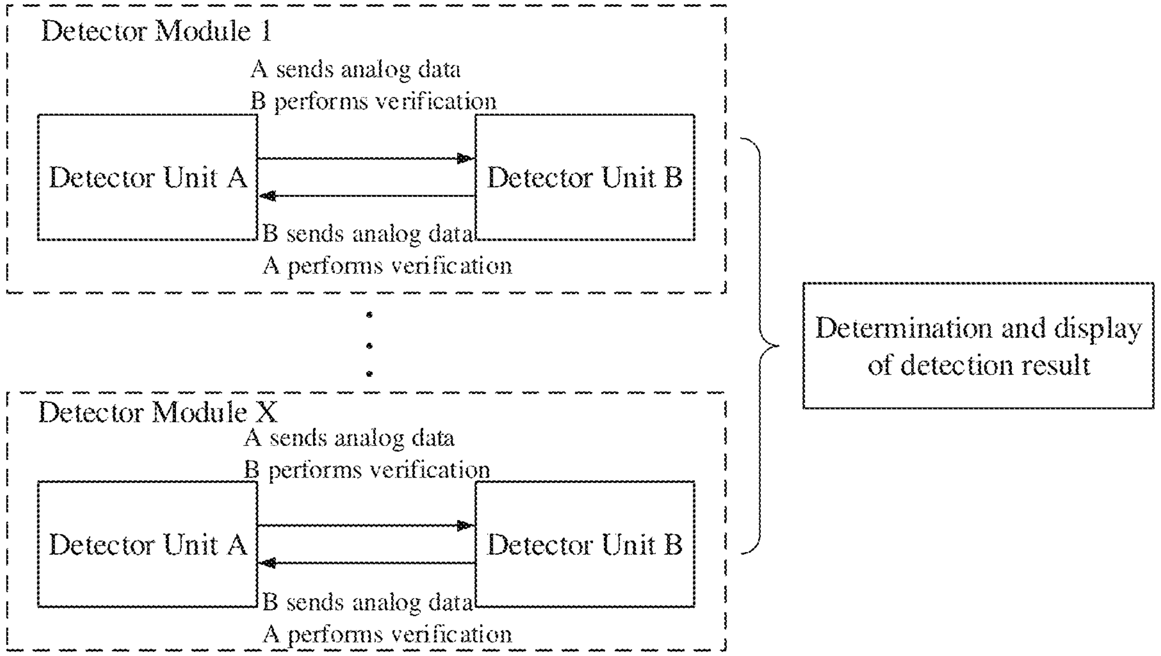
FIG. 4 is a schematic diagram illustrating a link structure of a detector data sub-link in an embodiment.

Referring to FIG. 4, the detector data sub-link may include at least one detector module, and each detector module may include a plurality of detector units. For each detector module, the detector units in the detector module may be connected to each other. Exemplarily, two detector units connected to each other may include a bidirectional data transmission link, or two unidirectional data transmission links. The detector module may refer to a detector ring, and each detector unit may refer to a detector in the detector ring.

As an example, referring to FIG. 4, the PET/CT system includes a plurality of detector rings arranged in an axial direction. The detector modules 1 to X are different detector rings in the PET/CT system, respectively. Each detector ring may include a detector unit A and a detector unit B. For example, the detector module 1 may include a detector unit A and a detector unit B. This embodiment refers to the detection of the coincidence event in the same detector ring. In a case that the data transmission link is a unidirectional data transmission link, there is a data transmission link between the detector unit A and the detector unit B, in which the detector unit A sends data to the detector unit B, and a data transmission link in which the detector unit B sends data to the detector unit A, i.e., there are two unidirectional data transmission links between the detector unit A and the detector unit B. In this case, the detector unit A in the detector module 1 may be taken as the sending component, and the detector unit B correspondingly connected to the detector unit A may be taken as the receiving component corresponding to the detector unit A. Alternatively, the detector unit B in the detector module 1 may be taken as the sending component, and the detector unit A correspondingly connected to the detector unit B may be taken as the receiving component corresponding to the detector unit B.

In other words, in a case that the target data sub-link is the detector data sub-link, for the detector units in each detector module, the detector unit in the detector module may be determined as the sending component, and another detector unit corresponding to the detector unit in the detector module may be determined as the receiving component corresponding to the sending component.

For example, in a case that the detector module 1 further includes three or more detector units such as detector unit C and detector unit D, a data transmission link may be included between the detector unit A and the detector unit B for sending data from the detector unit A to the detector unit B, a data transmission link may be included between the detector unit A and the detector unit C for sending data from the detector unit A to the detector unit C, and a data transmission link may be included between the detector unit A and the detector unit D for sending data from the detector unit A to the detector unit D. In this way, in a case that the detector unit A in the detector module 1 is taken as the sending component, the receiving components corresponding to the detector unit A may include the detector unit B, detector unit C and detector unit D in the detector module 1.

Using the same method, the corresponding receiving components may be determined in a case that the detector unit B in the detector module 1 is taken as the sending component, the corresponding receiving component may be determined in a case that the detector unit C in the detector module 1 is taken as the sending component, and the corresponding receiving component may be determined in a case that the detector unit D in the detector module 1 is taken as the sending component. The corresponding receiving component may also be determined in a case that each detector unit in other detector modules in the detector data sub-link is taken as the sending component.

Based on this, for each sending component determined in the detector data sub-link, the detection instruction may be sent to the sending component (i.e., each detector unit in each detector module), so as to instruct the sending component to send the detection data to one or more corresponding receiving components for detection.

Figure 5:
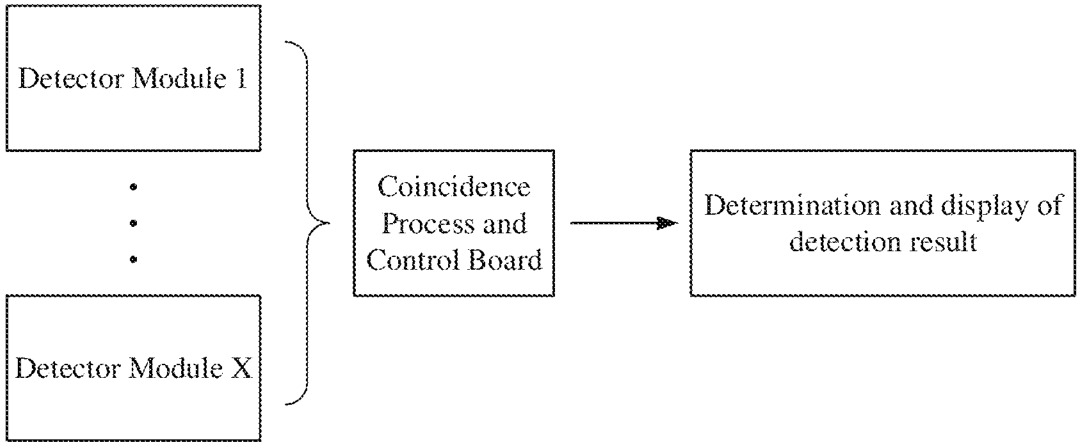
FIG. 5 is a schematic diagram illustrating a link structure of a coincidence process and control board data sub-link in an embodiment.

Referring to FIG. 5, the coincidence process and control board data sub-link may include at least one detector module and at least one coincidence process and control board (CCB) correspondingly connected to the at least one detector module. Exemplarily, one detector module may be connected to one coincidence process and control board, or a plurality of detector modules may be connected to one coincidence process and control board. In a case that there are a large number of detector modules, a plurality of coincidence process and control boards may also be provided. In this case, one coincidence process and control board is connected to a plurality of detector modules, and the detector modules connected to different coincidence process and control boards may be different. Based on this, a data transmission link formed by connecting at least one detector module to one coincidence process and control board may be referred to as the coincidence process and control board data sub-link, as shown in FIG. 5, and one or more coincidence process and control board data sub-links may be included in the PET data link. This embodiment also refers to the coincidence event detection in the same detector ring. The difference from the coincidence event detection in the detector ring mentioned above is that the detection data of each detector ring is sent to the corresponding coincidence process and control board for verification.

Exemplarily, in a case that the target data sub-link is the coincidence process and control board data sub-link, each coincidence process and control board data sub-link in the PET data link may be detected. For each coincidence process and control board data sub-link, each detector module in the coincidence process and control board data sub-link may be taken as the sending component, and the coincidence process and control board in the coincidence process and control board data sub-link may be taken as the receiving component corresponding to the sending component.

Take a link structure of the coincidence process and control board data sub-link shown in FIG. 5 as an example, the detector module 1 to the detector module X are each connected to the coincidence process and control board. In this case, the detector module 1 to the detector module X may be determined as sending components, and the coincidence process and control board may be determined as the receiving component corresponding to each detector module in the detector module 1 to the detector module X, i.e., the coincidence process and control board in the data transmission link may be taken as the receiving component corresponding to the detector module 1, as the receiving component corresponding to the detector module 2, and as the receiving component corresponding to the detector module X.

Further, the detection instruction may be sent to the detector module 1 to the detector module X, respectively, so as to instruct the detector module 1 to the detector module X to send preset detection data to the coincidence process and control board, respectively, thereby achieving the detection for the data transmission link between each detector module and the coincidence process and control board.

Figure 6:
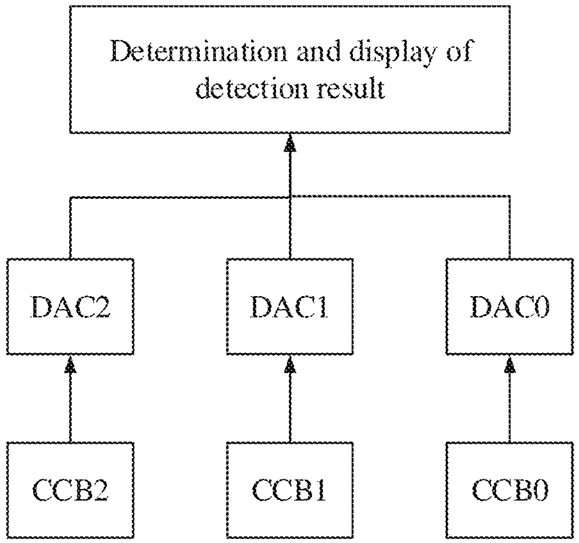
FIG. 6 is a schematic diagram illustrating a link structure of an acquisition card data sub-link in an embodiment.

Referring to FIG. 6, the acquisition card data sub-link may include at least one CCB and a data acquisition card (DAC) correspondingly connected to the at least one coincidence process and control board. Exemplarily, one coincidence process and control board may be connected to one data acquisition card, and a data transmission link between the coincidence process and control board and the data acquisition card may be referred to as the acquisition card data sub-link. One or more acquisition card data sub-links may be included in the PET data link.

Exemplarily, in a case that the target data sub-link is the acquisition card data sub-link, each acquisition card data sub-link in the PET data link can be detected. For each acquisition card data sub-link, the coincidence process and control board in the acquisition card data sub-link may be taken as the sending component, and the data acquisition card connected to the coincidence process and control board in the acquisition card data sub-link may be taken as the receiving component corresponding to the sending component.

In other examples, one data acquisition card may also be connected to a plurality of coincidence process and control boards. In this case, each coincidence process and control board may be taken as the sending component, and the data acquisition card correspondingly connected to the coincidence process and control board may be taken as the receiving component corresponding to the sending component.

Figure 7:
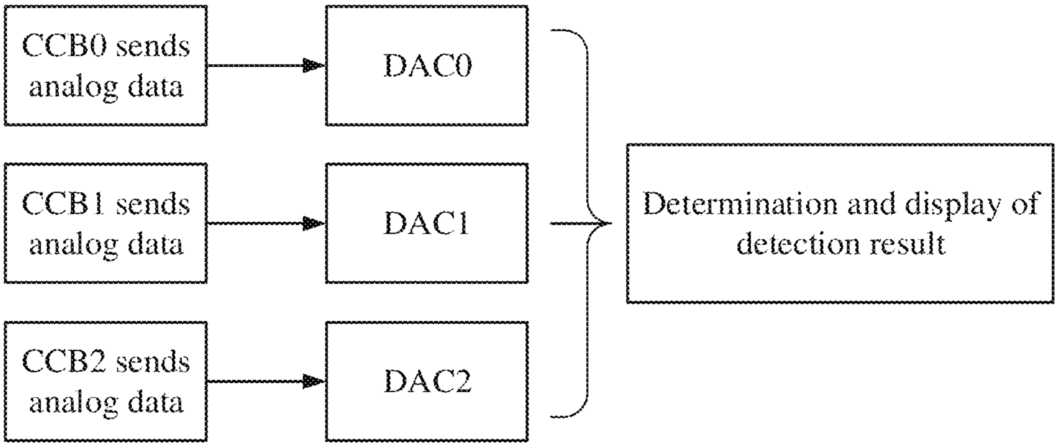
FIG. 7 is a schematic diagram of performing a data link detection on the acquisition card data sub-link shown in FIG. 6.

Taking a link structure of the acquisition card data sub-link shown in FIG. 6 as an example, the coincidence process and control board CCB0 is correspondingly connected to the data acquisition card DAC0, the coincidence process and control board CCB1 is correspondingly connected to the data acquisition card DAC1, and the coincidence process and control board CCB2 is correspondingly connected to the data acquisition card DAC2. Based on this, referring to FIG. 7, in a case that the coincidence process and control board CCB0 is taken as the sending component, the corresponding receiving component is the data acquisition card DAC0. In a case that the coincidence process and control board CCB1 is taken as the sending component, the corresponding receiving component is the data acquisition card DAC1. In a case that the coincidence process and control board CCB2 is taken as the sending component, the corresponding receiving component is the data acquisition card DAC2.

Figure 8:
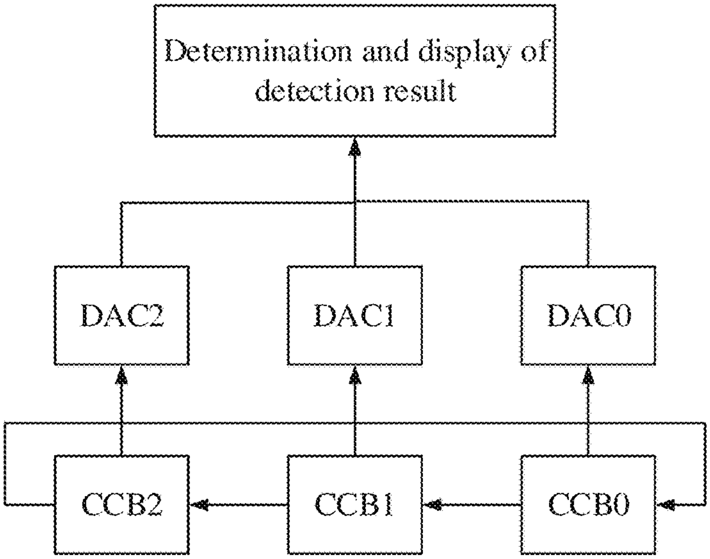
FIG. 8 is a schematic diagram illustrating a link structure of an acquisition card data sub-link in another embodiment.

Exemplarily, in some application scenarios, for the coincidence process and control boards in the acquisition card data sub-link, there may also be data transmission between the coincidence process and control boards. Exemplarily, the acquisition card data sub-link may include coincidence process and control boards that are communicatively connected in sequence. Referring to FIG. 8, the coincidence process and control board CCB0 is communicatively connected to the coincidence process and control board CCB1, the coincidence process and control board CCB1 is communicatively connected to the coincidence process and control board CCB2, and the coincidence process and control board CCB2 is communicatively connected to the coincidence process and control board CCB0. The CCB0, CCB1, and CCB2 correspond to different detector rings, respectively, and this data detection for CCBs corresponding to different detector rings is cross-ring coincidence detection. A bidirectional data transmission link may be used between the two coincidence process and control boards that are communicatively connected to each other, so as to achieve mutual data transmission between the two coincidence process and control boards that are communicatively connected to each other.

Based on this, for a link structure of the acquisition card data sub-link shown in FIG. 8, when a data link detection is performed, the coincidence process and control board may also be controlled to send the detection data to a coincidence process and control board adjacent to and communicatively connected to this coincidence process and control board, i.e., an adjacent coincidence process and control board, and then the detection data is sent to the data acquisition card correspondingly connected to the adjacent coincidence process and control board through the adjacent coincidence process and control board. In other words, for each of coincidence process and control boards in the acquisition card data sub-link, the coincidence process and control board may be determined as the sending component, and the acquisition card correspondingly connected to the adjacent coincidence process and control board that is communicatively connected to the coincidence process and control board may be determined as the receiving component corresponding to the sending component.

Figure 9:
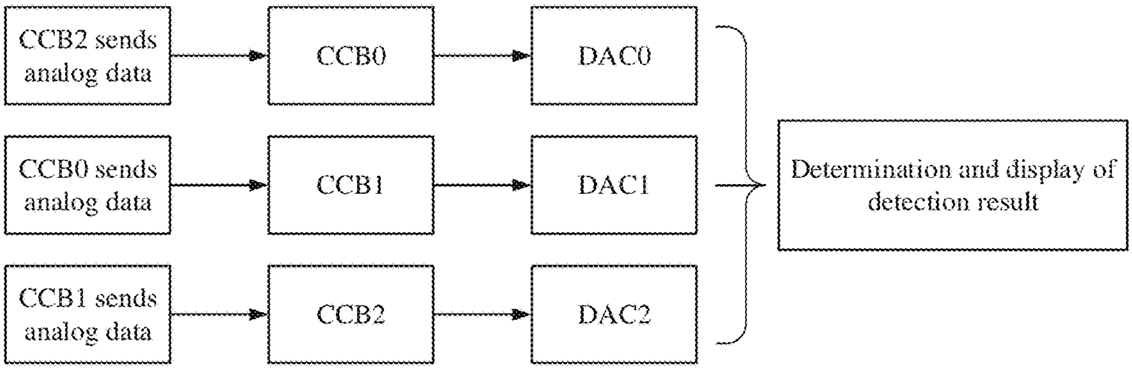
FIG. 9 is a schematic diagram of performing a data link detection on the acquisition card data sub-link shown in FIG. 8.

Exemplarily, referring to FIG. 9, in a case that the coincidence process and control board CCB0 is taken as the sending component, the data acquisition card DAC1 corresponding to the coincidence process and control board CCB1 which is adjacent to and communicatively connected to the coincidence process and control board CCB0 may be taken as the receiving component. In a case that the coincidence process and control board CCB1 is taken as the sending component, the data acquisition card DAC2 corresponding to the coincidence process and control board CCB2 which is adjacent to and communicatively connected to the coincidence process and control board CCB1 may be taken as the receiving component. In a case that the coincidence process and control board CCB2 is taken as the sending component, the data acquisition card DAC0 corresponding to the coincidence process and control board CCB0 which is adjacent to and communicatively connected to the coincidence process and control board CCB2 may be taken as the receiving component.

In this way, the coincidence process and control board CCB0 may first send preset detection data to the coincidence process and control board CCB1, and then the coincidence process and control board CCB1 may send the received detection data to the data acquisition card DAC1. After receiving the detection data, the data acquisition card DAC1 may determine the received detection data to obtain the detection result. It should be noted that the coincidence process and control board CCB0 may completely transparently transmit the detection data to the coincidence process and control board CCB1, i.e., the coincidence process and control board CCB0 does not process the detection data to be sent, but directly sends the detection data to the coincidence process and control board CCB1.

Similarly, the coincidence process and control board CCB1 may transparently transmit preset detection data to the coincidence process and control board CCB2, and then the coincidence process and control board CCB2 sends the received detection data to the data acquisition card DAC2. The coincidence process and control board CCB2 may transparently transmit preset detection data to the coincidence process and control board CCB0, and then the coincidence process and control board CCB0 sends the received detection data to the data acquisition card DAC0.

In another example, in a case that the coincidence process and control board CCB0 is taken as the sending component, the data acquisition card DAC2 corresponding to the coincidence process and control board CCB2 which is adjacent to and communicatively connected to the coincidence process and control board CCB0 may also be taken as the receiving component. In a case that the coincidence process and control board CCB2 is taken as the sending component, the data acquisition card DAC1 corresponding to the coincidence process and control board CCB1 which is adjacent to and communicatively connected to the coincidence process and control board CCB2 may be taken as the receiving component. In a case that the coincidence process and control board CCB1 is taken as the sending component, the data acquisition card DAC0 corresponding to the coincidence process and control board CCB0 which is adjacent to and communicatively connected to the coincidence process and control board CCB1 may be taken as the receiving component.

In addition, in another example, the data transmission link between adjacent coincidence process and control boards is a bidirectional data transmission link, i.e., in a case that the adjacent coincidence process and control board CCB0 sends data to the coincidence process and control board CCB1, and the coincidence process and control board CCB1 sends data to the coincidence process and control board CCB0, the same data transmission line is used. Therefore, in a case that the data transmission line between the coincidence process and control board CCB0 and the coincidence process and control board CCB1 is tested, only the coincidence process and control board CCB0 may send data to the coincidence process and control board CCB1 for testing, or only the coincidence process and control board CCB1 may send data to the coincidence process and control board CCB0 for testing.

In this way, on the basis of detecting the coincidence process and control board CCB0 and the corresponding data acquisition card DAC0, and the coincidence process and control board CCB1 and the corresponding data acquisition card DAC1, in a case that the data transmission link between the coincidence process and control board CCB0 and the coincidence process and control board CCB1 is detected, the coincidence process and control board CCB0 may be taken as the sending component and the data acquisition card DAC1 may be taken as the receiving component for testing, or the coincidence process and control board CCB1 may be taken as the sending component and the DAC0 may be taken as the receiving component for testing.

Similarly, the detection of the data transmission link between the coincidence process and control board CCB0 and the coincidence process and control board CCB2, and the detection of the data transmission link between the coincidence process and control board CCB1 and the coincidence process and control board CCB2 may refer to the detection method for the data transmission link between the coincidence process and control board CCB0 and the coincidence process and control board CCB1 described above, which will not describe repeatedly here.

In this embodiment, by analyzing the link structure of the target data sub-link, the sending components in different target data sub-links, and the receiving components corresponding to the sending components in the target data sub-links may be determined. Further, the detection instruction may be sent to the sending component in the target data sub-link to instruct the sending component to send the detection data to the corresponding receiving component for detection, thereby achieving the link detection for the target data sub-link. By using this method, automatic detection and control of different target data sub-links in the data link may be achieved, so that the stability and accuracy of the target data sub-link may be ensured when the target data sub-link for data transmission is used, thereby improving the accuracy and integrity of data transmission.

It should be understood that although the individual steps in the flow diagrams involved of the embodiments as described above are shown sequentially as indicated by arrows, the steps are not necessarily performed sequentially in the order indicated by the arrows. Unless explicitly stated herein, the execution of these steps is not strictly limited in order and these steps can be performed in any other order. Moreover, at least some of the steps in the flow diagrams involved of the embodiments as described above may include a plurality of steps or a plurality of stages that are not necessarily performed at the same time, but may be performed at different times. The order in which these steps or stages are performed is not necessarily sequential, and these steps may be performed alternately or alternately with other steps or at least some of the steps or stages in other steps.

Based on the same inventive concept, embodiments of the present disclosure also provide a data link detection device for implementing the data link detection method as described above. The solution to the problem provided by the device is similar to the implementation of the method documented above, so the specific features in the one or more embodiments of the data link detection device provided below may be understood with reference to the features of the data link detection method above and will not be repeated here.

Figure 10:
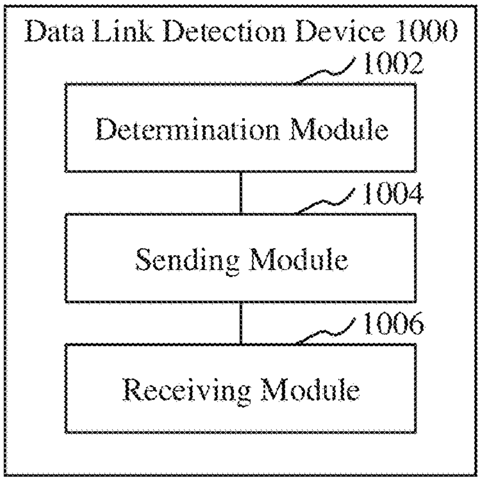
FIG. 10 is a block diagram illustrating a configuration of a data link detection device in an embodiment.

In an exemplary embodiment, as shown in FIG. 10, a data link detection device is provided. The data link detection device includes a determination module 1002, a sending module 1004 and a receiving module 1006. The determination module 1002 is configured to determine a target data sub-link in a data link. The data link includes at least one data sub-link. The sending module 1004 is configured to send a detection instruction to a sending component in the target data sub-link to instruct the sending component to send detection data to a receiving component in the target data sub-link for detection. The receiving module 1006 is configured to receive a detection result corresponding to the target data sub-link.

In an embodiment, the data link includes a detector data sub-link, a coincidence process and control board data sub-link, and an acquisition card data sub-link. The detector data sub-link includes at least one detector module, and each detector module includes a plurality of detector units. The coincidence process and control board data sub-link includes the at least one detector module and at least one coincidence process and control board correspondingly connected to the at least one detector module. The acquisition card data sub-link includes at least one coincidence process and control board and at least one data acquisition card connected to the at least one coincidence process and control board respectively.

In an embodiment, the sending module 1004 includes: a determination submodule configured to determine the sending component in the target data sub-link and the receiving component corresponding to the sending component in the target data sub-link; and a sending submodule configured to send the detection instruction to the sending component to instruct the sending component to send the detection data to the corresponding receiving component for detection.

In an embodiment, the target data sub-link is the detector data sub-link, the determination submodule includes: a first determination unit configured to determine, for the plurality of detector units in each detector module, a detector unit in the detector module as the sending component; and a second determination unit configured to determine another detector unit corresponding to the detector unit in the detector module as the receiving component corresponding to the sending component.

In an embodiment, the target data sub-link is the coincidence process and control board data sub-link, the determination submodule includes: a third determination unit configured to determine, for each detector module, the detector module as the sending component; and a fourth determination unit configured to determine the coincidence process and control board connected to the detector module as the receiving component corresponding to the sending component.

In an embodiment, the target data sub-link is the acquisition card data sub-link, the determination submodule includes: a fifth determination unit configured to determine, for each coincidence process and control board, the coincidence process and control board as the sending component; and a sixth determination unit configured to determine the acquisition card connected to the coincidence process and control board as the receiving component corresponding to the sending component.

In an embodiment, the target data sub-link is the acquisition card data sub-link, and the acquisition card data sub-link includes coincidence process and control boards that are communicatively connected in sequence, the determination submodule includes: a seventh determination unit configured to determine, for each coincidence process and control board, the coincidence process and control board as the sending component; an eighth determination unit configured to determine an adjacent coincidence process and control board adjacent to and communicatively connected to the coincidence process and control board; and a ninth determination unit configured to determine the acquisition card connected to the adjacent coincidence process and control board as the receiving component corresponding to the sending component.

The individual modules in the above data link detection device can be implemented in whole or in part by software, hardware and combinations thereof. Each of the above modules may be embedded in hardware form or independent of a processor in a computer device, or may be stored in software form on a memory in the computer device so that the processor can be called to perform the operations corresponding to each of the above modules.

Figure 12:
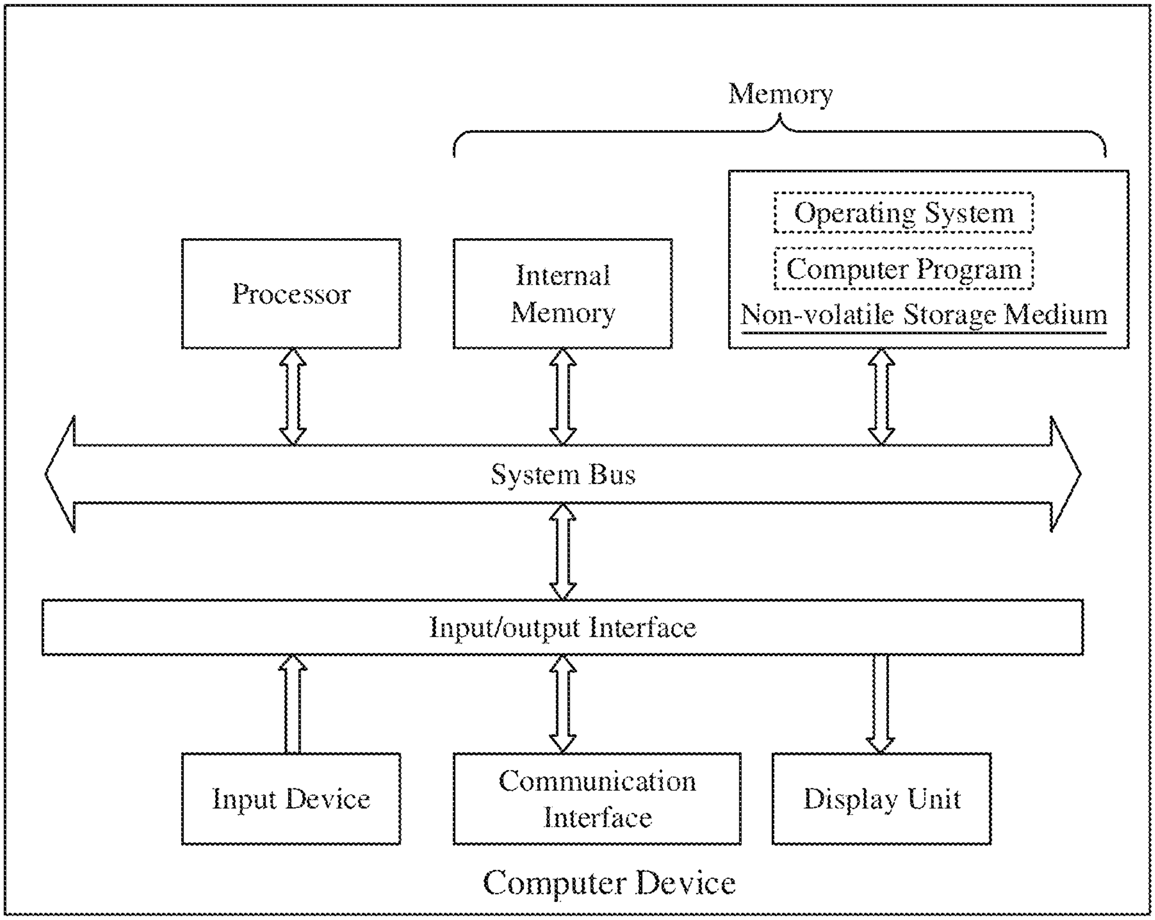
FIG. 12 is a diagram illustrating an internal configuration of a computer device in an embodiment.

In an exemplary embodiment, a computer device is provided. The computer device may be a data acquisition device or a data storage device. The computer device may be used to detect and control a data transmission link between the data acquisition device and the data storage device. FIG. 12 illustrates an internal configuration of the computer device. The computer device includes a processor, a memory, an input/output interface, a communication interface, a display unit, and an input device. The processor, the memory and the input/output interface are connected via a system bus, and the communication interface, the display unit and the input device are connected to the system bus via the input/output interface. The processor of the computer device is configured to provide computing and control capabilities. The memory of the computer device includes a non-transitory storage medium and an internal memory. The non-transitory storage medium stores operating systems and computer programs. The internal memory provides an environment for the operation of the operating systems and the computer programs in the non-transitory storage medium. The input/output interface of the computer device is configured to exchange information between the processor and external devices. The communication interface of the computer device is configured to communicate with external terminals in wired or wireless mode, which can be realized by WIFI, mobile cellular network, near field communication (NFC) or other technologies. The computer programs are executed by the processor in order to implement a data link detection method. The display unit of the computer device is configured to form a visually visible picture, which may be a display screen, a projection device or a virtual reality imaging device. The display screen may be an LCD or e-ink display, and the input device of the computer device may be a touch layer covered by the display screen, or a key, trackball or trackpad set on the housing of the computer device, or an external keyboard, trackpad or mouse, etc.

It should be understood by a person of ordinary skill in the art that the configuration illustrated in FIG. 12, which is only a block diagram of part of the configuration related to the solution of the present disclosure, and does not constitute a limitation on the computer device to which the solution of the present disclosure is applied. Specifically, the computer device may include more or less components than those shown in the figure, or may combine some components, or may have a different arrangement of components.

Figure 11:
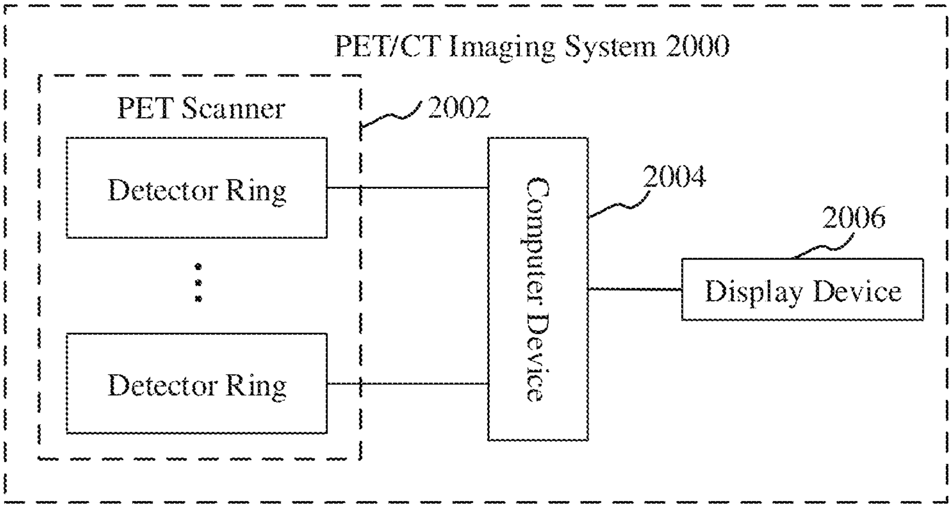
FIG. 11 is a block diagram illustrating a configuration of a PET/CT imaging system in an embodiment.

In an exemplary embodiment, a PET/CT imaging system 2000 is provided. As shown in FIG. 11, the PET/CT imaging system 2000 includes a PET scanner 2002, a computer device 2004, and a display device 2006. The PET scanner 2002 includes a plurality of detector rings arranged in an axial direction, and each detector ring is connected to the computer device 2004 via a data link.

In an exemplary embodiment, a computer device is provided. The computer device includes a processor and a memory storing a computer program. When the processor executes the computer program, steps of the data link detection method in any one of the above embodiments are implemented. The detection result is sent to the display device 2006 for display.

In an embodiment, a non-transitory computer-readable storage medium is provided. The non-transitory computer-readable storage medium has a computer program stored therein. When the computer program is executed by a processor, steps of the data link detection method in any one of the above embodiments are implemented.

In an embodiment, a computer program product is provided. The computer program product includes a computer program. When the computer program is executed by a processor, steps of the data link detection method in any one of the above embodiments are implemented.

It should be noted that the user information (including but not limited to user device information, user personal information, etc.) and data (including but not limited to data used for analysis, stored data, displayed data, etc.) involved in the present disclosure are information and data authorized by the user or fully authorized by all parties, and the collection, use and processing of relevant data need to comply with relevant regulations.

A person of ordinary skill in the art may understand that implementation of all or part of the processes in the methods of the above embodiments may be completed by instructing the relevant hardware through a computer program. The computer program may be stored in a non-transitory computer-readable storage medium. When the computer program is executed, it may include the processes of the embodiments of the above methods. Any reference to memory, database or other medium used of the embodiments provided in the present disclosure may include at least one of a non-transitory and a transitory memory. The non-transitory memory may include a read-only memory (ROM), a magnetic tape, a floppy disk, a flash memory, an optical memory, a high-density embedded non-transitory memory, a resistive random-access memory (ReRAM), a magneto resistive random-access memory (MRAM), a ferroelectric random-access memory (FRAM), a phase change memory (PCM), or a graphene memory, etc. The transitory memory may include a random-access memory (RAM) or an external cache memory, etc. As an illustration rather than a limitation, the random-access memory may be in various forms, such as a static random-access memory (SRAM) or a dynamic random-access memory (DRAM), etc. The databases involved of the embodiments provided by the present disclosure may include at least one of a relational database and a non-relational database. The non-relational database may include, but is not limited to, a blockchain-based distributed database, etc. The processor involved of the embodiments provided by the present disclosure may be, but is not limited to, a general purpose processor, a central processor, a graphics processor, a digital signal processor, a programmable logic device, a data processing logic device based on quantum computation, and the like.

The technical features in the above embodiments may be combined arbitrarily. For concise description, not all possible combinations of the technical features in the above embodiments are described. However, provided that they do not conflict with each other, all combinations of the technical features are to be considered to be within the scope described in this specification.

The above-mentioned embodiments only describe several implementations of the present disclosure, and their description is specific and detailed, but should not be understood as a limitation on the patent scope of the present disclosure. It should be noted that, for a person of ordinary skill in the art may further make variations and improvements without departing from the conception of the present disclosure, and these all fall within the protection scope of the present disclosure. Therefore, the protection scope of the present disclosure should be subject to the appended claims.

What is claimed is:

1. A data link detection method for a PET/CT imaging system, the PET/CT imaging system including a plurality of detector rings, the method comprising:

determining a target data sub-link in a data link, the data link comprising at least one data sub-link, the at least one data sub-link corresponding to a coincidence event belonging to a single detector ring or to a coincidence event belonging to different detector rings;

sending a detection instruction to a sending component in the target data sub-link to instruct the sending component to send detection data to a receiving component in the target data sub-link for detection; and receiving a detection result corresponding to the target data sub-link.

2. The method of claim 1, wherein:

the data link comprises a detector data sub-link, a coincidence process and control board data sub-link, and an acquisition card data sub-link;

the detector data sub-link comprises at least one detector module, and each detector module comprises a plurality of detector units;

the coincidence process and control board data sub-link comprises the at least one detector module and at least one coincidence process and control board correspondingly connected to the at least one detector module; and the acquisition card data sub-link comprises the at least one coincidence process and control board and at least one data acquisition card connected to the at least one coincidence process and control board respectively.

3. The method of claim 2, wherein sending the detection instruction to the sending component in the target data sub-link to instruct the sending component to send the detection data to the receiving component in the target data sub-link for detection, comprises:

determining the sending component in the target data sub-link and the receiving component corresponding to the sending component in the target data sub-link; and sending the detection instruction to the sending component to instruct the sending component to send the detection data to the corresponding receiving component for detection.

4. The method of claim 3, wherein the target data sub-link is the detector data sub-link, determining the sending component in the target data sub-link and the receiving component corresponding to the sending component in the target data sub-link comprises:

determining, for the plurality of detector units in each detector module, a detector unit in the detector module as the sending component; and determining another detector unit corresponding to the detector unit in the detector module as the receiving component corresponding to the sending component.

5. The method of claim 3, wherein the target data sub-link is the coincidence process and control board data sub-link, determining the sending component in the target data sub-link and the receiving component corresponding to the sending component in the target data sub-link comprises:

determining, for each detector module, the detector module as the sending component; and determining the coincidence process and control board connected to the detector module as the receiving component corresponding to the sending component.

6. The method of claim 3, wherein the target data sub-link is the acquisition card data sub-link, determining the sending component in the target data sub-link and the receiving component corresponding to the sending component in the target data sub-link comprises:

determining, for each coincidence process and control board, the coincidence process and control board as the sending component; and determining the acquisition card connected to the coincidence process and control board as the receiving component corresponding to the sending component.

7. The method of claim 3, wherein the target data sub-link is the acquisition card data sub-link, and the acquisition card data sub-link comprises coincidence process and control boards that are communicatively connected in sequence, determining the sending component in the target data sub-link and the receiving component corresponding to the sending component in the target data sub-link comprises:

determining, for each coincidence process and control board, the coincidence process and control board as the sending component;

determining an adjacent coincidence process and control board adjacent to and communicatively connected to the coincidence process and control board; and determining the acquisition card connected to the adjacent coincidence process and control board as the receiving component corresponding to the sending component.

8. A PET/CT imaging system, comprising a PET scanner, a computer device, and a display device;

the PET scanner comprising a plurality of detector rings arranged in an axial direction, and each detector ring being connected to the computer device via a data link;

the computer device comprising a processor and a memory storing a computer program, wherein when the processor executes the computer program, the processor is caused to:

determine a target data sub-link in the data link, the data link comprising at least one data sub-link;

send a detection instruction to a sending component in the target data sub-link to instruct the sending component to send detection data to a receiving component in the target data sub-link for detection; and receive a detection result corresponding to the target data sub-link, and send the detection result to the display device for display.

9. The PET/CT imaging system of claim 8, wherein:

the data link comprises a detector data sub-link, a coincidence process and control board data sub-link, and an acquisition card data sub-link;

the detector data sub-link comprises at least one detector module, and each detector module comprises a plurality of detector units;

the coincidence process and control board data sub-link comprises the at least one detector module and at least one coincidence process and control board correspondingly connected to the at least one detector module; and the acquisition card data sub-link comprises the at least one coincidence process and control board and at least one data acquisition card connected to the at least one coincidence process and control board respectively.

10. The PET/CT imaging system of claim 9, wherein when the processor executes the computer program, the processor is further caused to:

determine the sending component in the target data sub-link and the receiving component corresponding to the sending component in the target data sub-link; and send the detection instruction to the sending component to instruct the sending component to send the detection data to the corresponding receiving component for detection.

11. The PET/CT imaging system of claim 10, wherein the target data sub-link is the detector data sub-link, when the processor executes the computer program, the processor is further caused to:

determine, for the plurality of detector units in each detector module, a detector unit in the detector module as the sending component; and determine another detector unit corresponding to the detector unit in the detector module as the receiving component corresponding to the sending component.

12. The PET/CT imaging system of claim 10, wherein the target data sub-link is the coincidence process and control board data sub-link, when the processor executes the computer program, the processor is further caused to:

determine, for each detector module, the detector module as the sending component; and determine the coincidence process and control board connected to the detector module as the receiving component corresponding to the sending component.

13. The PET/CT imaging system of claim 10, wherein the target data sub-link is the acquisition card data sub-link, when the processor executes the computer program, the processor is further caused to:

determine, for each coincidence process and control board, the coincidence process and control board as the sending component; and determine the acquisition card connected to the coincidence process and control board as the receiving component corresponding to the sending component.

14. The PET/CT imaging system of claim 10, wherein the target data sub-link is the acquisition card data sub-link, and the acquisition card data sub-link comprises coincidence process and control boards that are communicatively connected in sequence, when the processor executes the computer program, the processor is further caused to:

determine, for each coincidence process and control board, the coincidence process and control board as the sending component;

determine an adjacent coincidence process and control board adjacent to and communicatively connected to the coincidence process and control board; and determine the acquisition card connected to the adjacent coincidence process and control board as the receiving component corresponding to the sending component.

15. A non-transitory computer-readable storage medium having a computer program stored therein, wherein when the computer program is executed by a processor, the processor is caused to:

determine a target data sub-link in a data link, the data link comprising at least one data sub-link;

send a detection instruction to a sending component in the target data sub-link to instruct the sending component to send detection data to a receiving component in the target data sub-link for detection; and receive a detection result corresponding to the target data sub-link.

16. The non-transitory computer-readable storage medium of claim 15, wherein:

the data link comprises a detector data sub-link, a coincidence process and control board data sub-link, and an acquisition card data sub-link;

the detector data sub-link comprises at least one detector module, and each detector module comprises a plurality of detector units;

the coincidence process and control board data sub-link comprises the at least one detector module and at least one coincidence process and control board correspondingly connected to the at least one detector module; and the acquisition card data sub-link comprises the at least one coincidence process and control board and at least one data acquisition card connected to the at least one coincidence process and control board respectively.

17. The non-transitory computer-readable storage medium of claim 16, wherein when the computer program is executed by a processor, the processor is caused to:

determine the sending component in the target data sub-link and the receiving component corresponding to the sending component in the target data sub-link; and send the detection instruction to the sending component to instruct the sending component to send the detection data to the corresponding receiving component for detection.

18. The non-transitory computer-readable storage medium of claim 17, wherein the target data sub-link is the detector data sub-link, when the computer program is executed by a processor, the processor is caused to:

determine, for the plurality of detector units in each detector module, a detector unit in the detector module as the sending component; and determine another detector unit corresponding to the detector unit in the detector module as the receiving component corresponding to the sending component.

19. The non-transitory computer-readable storage medium of claim 17, wherein the target data sub-link is the coincidence process and control board data sub-link, when the computer program is executed by a processor, the processor is caused to:

determine, for each detector module, the detector module as the sending component; and determine the coincidence process and control board connected to the detector module as the receiving component corresponding to the sending component.

20. The non-transitory computer-readable storage medium of claim 17, wherein the target data sub-link is the acquisition card data sub-link, when the computer program is executed by a processor, the processor is caused to:

determine, for each coincidence process and control board, the coincidence process and control board as the sending component; and determine the acquisition card connected to the coincidence process and control board as the receiving component corresponding to the sending component.

* * * * *